(12) United States Patent
Sundararajan et al.

(10) Patent No.: US 11,556,508 B1
(45) Date of Patent: Jan. 17, 2023

(54) MACHINE LEARNING SYSTEM FOR AUTOMATED ATTRIBUTE NAME MAPPING BETWEEN SOURCE DATA MODELS AND DESTINATION DATA MODELS

(71) Applicant: Cigna Intellectual Property, Inc., Wilmington, DE (US)

(72) Inventors: Lakshminarasimhan Sundararajan, Bridgewater, NJ (US); Prabhakar Goel, Highlands Ranch, CO (US)

(73) Assignee: Cigna Intellectual Property, Inc., Wilmington, DE (US)

( * ) Notice: Subject to any disclaimer, the term of this patent is extended or adjusted under 35 U.S.C. 154(b) by 255 days.

(21) Appl. No.: 16/895,163

(22) Filed: Jun. 8, 2020

(51) Int. Cl.
| | | |
|---|---|---|
| *G06F 16/00* | (2019.01) | |
| *G06F 16/21* | (2019.01) | |
| *G06F 40/242* | (2020.01) | |
| *G06N 3/04* | (2006.01) | |
| *G06F 16/28* | (2019.01) | |
| *G06N 20/00* | (2019.01) | |
| *G16H 40/20* | (2018.01) | |

(52) U.S. Cl.
CPC ......... *G06F 16/213* (2019.01); *G06F 16/283* (2019.01); *G06F 40/242* (2020.01); *G06N 3/04* (2013.01); *G06N 20/00* (2019.01); *G16H 40/20* (2018.01)

(58) Field of Classification Search
None
See application file for complete search history.

(56) References Cited

U.S. PATENT DOCUMENTS

| | | | | |
|---|---|---|---|---|
| 6,167,405 | A | * 12/2000 | Rosensteel, Jr. | ...... G06F 16/283 707/999.102 |
| 9,251,225 | B2 | * 2/2016 | Stanfill | ................... G06F 16/25 |
| 10,558,629 | B2 | 2/2020 | Yamashita | |
| 10,637,744 | B2 | 4/2020 | Carroll | |
| 2014/0258002 | A1 | 9/2014 | Zimmerman | |
| 2016/0142266 | A1 | 5/2016 | Carroll | |
| 2017/0308808 | A1 | 10/2017 | Kobylkin | |
| 2017/0316345 | A1 | * 11/2017 | Palmer | .................. G06F 16/951 |

(Continued)

OTHER PUBLICATIONS

Automated Mapping for Semantic-based Conversion of Transportation Data Formats, Hosseini et al., (Year: 2019).*

*Primary Examiner* — Jean M Corrielus
(74) *Attorney, Agent, or Firm* — Miller Johnson (57) ABSTRACT

A computer-implemented method of mapping attribute names of a source data model to a destination data model includes obtaining multiple source attribute names from the source data model, and obtaining multiple destination attribute names from the destination data model. The destination data model includes multiple attributes that correspond to attributes in the source data model having different attribute names. The method includes processing the obtained source attribute names and the obtained destination attribute names to standardize the attribute names according to specified character formatting, supplying the standardized attribute names to a machine learning network model to predict a mapping of each source attribute name to a corresponding one of the destination attribute names, and outputting, according to mapping results of the machine learning network model, an attribute mapping table indicating the predicted destination attribute name corresponding to each source attribute name.

16 Claims, 6 Drawing Sheets

(56) References Cited

U.S. PATENT DOCUMENTS

| | | |
|---|---|---|
| 2018/0032537 A1 | 2/2018 | Foley |
| 2018/0089574 A1 | 3/2018 | Goto |
| 2018/0349986 A1 | 12/2018 | Fidanza |
| 2018/0365578 A1* | 12/2018 | Naughton ............... G06N 5/022 |
| 2019/0102697 A1 | 4/2019 | Casalonga |
| 2019/0279101 A1* | 9/2019 | Habti .................. G06F 16/2456 |
| 2019/0332968 A1* | 10/2019 | Fu .............................. G06F 8/33 |
| 2020/0349130 A1* | 11/2020 | Bracholdt ........... G06F 16/2282 |

\* cited by examiner

FIG. 1 (System)

FIG. 2 (Lineage Map)

FIG. 3 (Attribute Mapping)

FIG. 4 (Mapping Table)

FIG. 5 (Neural Network)

FIG. 6 (Message Chart)

MACHINE LEARNING SYSTEM FOR AUTOMATED ATTRIBUTE NAME MAPPING BETWEEN SOURCE DATA MODELS AND DESTINATION DATA MODELS

FIELD

The present disclosure relates to machine learning for attribute name mapping between source data models and destination data models.

BACKGROUND

In the field of computing, many scenarios involve a distribution of data over a set of components, such as a set of servers that are connected by one or more networks. As an example, a cluster of servers may be arranged in a distributed system to store one or more distributed databases, where each server of the cluster stores a subset of the database(s), such as a subset of the tables of the database(s) and/or a subset of the records of a table of the database(s).

Many different database schemas may be aggregated into the distributed system, and each database schemas may provide different roles, store different data, etc. Each database schema may include one or more data models, with each data model having its own data with different representations, different attribute names, etc. In such a distributed system, difficulties may arise due to different data representations and attribute names among the data models, leading to problems in data transfer and communication between the data models, lack of understanding for system administrators, etc.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computer-implemented method of mapping attribute names of a source data model to a destination data model includes obtaining multiple source attribute names from the source data model, and obtaining multiple destination attribute names from the destination data model. The destination data model includes multiple attributes that correspond to attributes in the source data model having different attribute names. The method includes processing the obtained source attribute names and the obtained destination attribute names to standardize the attribute names according to specified character formatting, supplying the standardized attribute names to a machine learning network model to predict a mapping of each source attribute name to a corresponding one of the destination attribute names, and outputting, according to mapping results of the machine learning network model, an attribute mapping table indicating the predicted destination attribute name corresponding to each source attribute name.

In other features, the method includes, in response to determining that the machine learning network model was unable to predict a mapping for one of the source attribute names, receiving a matching input from a user identifying one of the destination attribute names that corresponds to an unmapped source attribute name, and updating a custom dictionary to include the matching input received from the user. In other features, supplying the standardized attribute names to a machine learning network model includes determining whether any of the source attribute names have an existing entry in the custom dictionary. For each source attribute name that has an existing entry in the custom dictionary, the method includes recording an output mapping for the source attribute name according to the existing entry in the custom dictionary. For each source attribute name that does not have an existing entry in the custom dictionary, the method includes using the machine learning network model to predict a mapping of the source attribute name to a corresponding one of the destination attribute names.

In other features, the method includes repeating multiple cycles of processing each source attribute name by predicting a corresponding destination attribute name using the machine learning network model or identifying a matching existing entry in the custom dictionary, until the attribute mapping table includes a mapped destination attribute name for a threshold number of source attribute names. In other features, the threshold number of source attribute names includes one hundred percent of the source attribute names.

In other features, supplying the standardized attribute names to a machine learning network model includes selecting a first one of the source attribute names and using the machine learning network model to identify one of the destination attribute names having a highest likelihood of correspondence with the selected first source attribute name, recording a mapping of the selected first source attribute name to the identified destination attribute name, and iteratively proceeding through the remaining source attribute names to identify and record a corresponding destination attribute name for each source attribute name and returning a match percentage based on a confidence interval.

In other features, processing the obtained source attribute names and the obtained destination attribute names to standardize the attribute names includes at least one of removing camel cases from the source attribute names and the destination attribute names, removing spaces from the source attribute names and the destination attribute names, removing underscores from the source attribute names and the destination attribute names, and removing special characters from the source attribute names and the destination attribute names.

In other features, the machine learning network model includes a natural language processing (NLP)-based algorithm. In other features, the machine learning network model includes a long short-term memory (LSTM) network. In other features, the source data model and the destination data model belong to different database schemas within a distributed data storage system. In other features, the source data model belongs to one of a data lake bounded context and a de-normalized data zone bounded context of a health care publisher platform, and the destination model belongs to one of the de-normalized data zone bounded context and a subscribing client entity bounded context of the health care publisher platform.

In other features, a computer system includes memory configured to store a source data model, a destination data model, a machine learning network model, and computer-executable instructions, and at least one processor configured to execute the instructions. The instructions include obtaining multiple source attribute names from the source data model, and obtaining multiple destination attribute names from the destination data model. The destination data model includes multiple attributes that correspond to attributes in the source data model having different attribute names. The method includes processing the obtained source attribute names and the obtained destination attribute names to standardize the attribute names according to specified character formatting, supplying the standardized attribute names to a machine learning network model to predict a mapping of each source attribute name to a corresponding one of the destination attribute names, and outputting, according to mapping results of the machine learning network model, an attribute mapping table indicating the predicted destination attribute name corresponding to each source attribute name.

In other features, the instructions include, in response to determining that the machine learning network model was unable to predict a mapping for one of the source attribute names, receiving a matching input from a user identifying one of the destination attribute names that corresponds to an unmapped source attribute name, and updating a custom dictionary to include the matching input received from the user. In other features, supplying the standardized attribute names to a machine learning network model includes determining whether any of the source attribute names have an existing entry in a custom dictionary. For each source attribute name that has an existing entry in the custom dictionary, the instructions include recording an output mapping for the source attribute name according to the existing entry in the custom dictionary. For each source attribute name that does not have an existing entry in the custom dictionary, the instructions include using the machine learning network model to predict a mapping of the source attribute name to a corresponding one of the destination attribute names.

In other features, the instructions include repeating multiple cycles of processing each source attribute name by predicting a corresponding destination attribute name using the machine learning network model or identifying a matching existing entry in the custom dictionary, until the attribute mapping table includes a mapped destination attribute name for a threshold number of source attribute names. In other features, the threshold number of source attribute names includes one hundred percent of the source attribute names.

In other features, supplying the standardized attribute names to a machine learning network model includes selecting a first one of the source attribute names and using the machine learning network model to identify one of the destination attribute names having a highest likelihood of correspondence with the selected first source attribute name, recording a mapping of the selected first source attribute name to the identified destination attribute name, and iteratively proceeding through the remaining source attribute names to identify and record a corresponding destination attribute name for each source attribute name and returning a match percentage based on a confidence interval.

In other features, processing the obtained source attribute names and the obtained destination attribute names to standardize the attribute names includes at least one of removing camel cases from the source attribute names and the destination attribute names, removing spaces from the source attribute names and the destination attribute names, removing underscores from the source attribute names and the destination attribute names, and removing special characters from the source attribute names and the destination attribute names.

In other features, the source data model and the destination model belong to different database schemas within a distributed data storage system. In other features, the source data model belongs to one of a data lake bounded context and a de-normalized data zone bounded context of a health care publisher platform, and the destination model belongs to one of the de-normalized data zone bounded context and a subscribing client entity bounded context of the health care publisher platform.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

In various implementations, a complex distributed data system may include multiple database schemas that each have data models using different data representations, different attribute names, etc. An attribute name mapping model may be used to compare attribute names across source and destination models. A source model and a destination model are provide as inputs, and the attribute name mapping model makes a prediction to map each attribute name in the source model to an attribute name in the destination model. The predictions may be based on natural language processing (NLP) models, logic, etc. As an output, the attribute name mapping model may provide a list of attribute name mappings between the source and destination models.

For example, a publisher platform may obtain data from disparate sources (e.g., data lakes, de-normalized data zones, etc.) and transform the data before loading it to a target destination (e.g., subscribing client entities, etc.). Similar or same data may be stored in multiple ones of the disparate sources, but may use different attribute names in the database schemas of each source. The attribute name mapping model may be used to map attribute names from a source model in one database schema, to a destination model in another database schema.

As described further below, the attribute name mapping model may first standardize (e.g., clean) model data by processing camel cases, spaces, underscores, special characters, etc. A machine learning algorithm (e.g., an NLP-based fuzzy logic algorithm) iterates through each standardized attribute name in the source model and determines a best standardized attribute name match from the destination model.

During the mapping process, a custom dictionary may be referred to in order to determine whether an exact match exists. The custom dictionary may be updated after the process iterates through each attribute name, in order to improve attribute name matching for subsequent iterations through the source model attribute names. For example, a system administrator may manually update the dictionary for source attribute names that received a poor matching prediction. After the attribute mapping model has proceed through the source model attribute names a specified number of times, reached a percentage threshold of mapped attribute names, etc., an output mapping table is generated that can be consumed by an application calling the application mapping model, viewed by a system administrator, etc.

Attribute Name Mapping System

Figure 1:
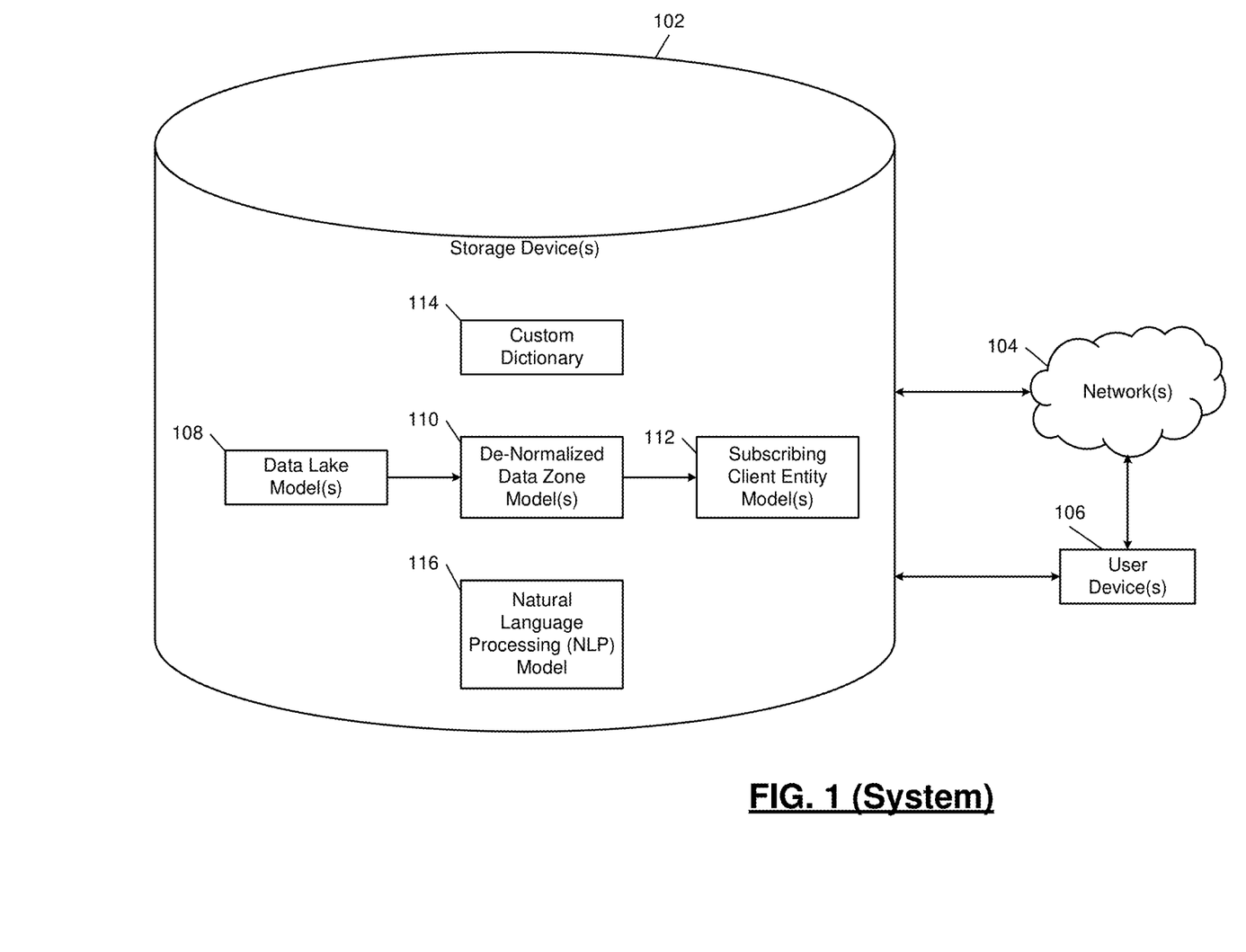
FIG. 1 is a functional block diagram of an example system for mapping attribute names between source and destination models.

FIG. 1 is a block diagram of an example implementation of a system for mapping attribute names between a source model and a destination model, including a storage device 102. While the storage device 102 is generally described as being deployed in a computer network system, the storage device 102 and/or components of the storage device 102 may otherwise be deployed (for example, as a standalone computer setup, etc.). The storage device 102 may be a desktop computer, a laptop computer, a tablet, a smartphone, etc.

As shown in FIG. 1, the storage device 102 includes data lake model(s) 108 (e.g., external chaos bounded contexts, etc.), de-normalized data zone model(s) 110 (e.g., internal bounded contexts, etc.), and subscribing client entity data model(s) 112 (e.g., consumer view bounded contexts, etc.). The data lake model(s) 108, de-normalized data zone model(s) 110, and subscribing client entity model(s) 112 may be located in different physical memories within the storage device 102, such as different random access memory (RAM), read-only memory (ROM), a non-volatile hard disk or flash memory, etc. In some implementations, one or more of the data lake model(s) 108, de-normalized data zone model(s) 110, and subscribing client entity model(s) 112 may be located in the same memory (e.g., in different address ranges of the same memory, etc.).

The storage device 102 may be part of a publisher platform including multiple database schemas (e.g., bounded contexts, etc.), where each of the data lake model(s) 108, de-normalized data zone model(s) 110, and subscribing client entity model(s) 112 belong to different ones of the multiple database schemas. For example, the data lake data model(s) 108 may be considered as chaos bounded contexts that provide data from disparate data sources, the de-normalized data zone model(s) 110 may be considered as intermediate transformation bounded contexts, and the subscribing client entity data model(s) 112 may be considered as bounded contexts that format the transformed source data for output presentation to a consumer (e.g., a subscribing client entity that requires data conforming to a specified format, etc.).

A distributed data set stored across the data lake model(s) 108, de-normalized data zone model(s) 110, and subscribing client entity model(s) 112, may include data from a patient population of a healthcare system, and each component of the system of FIG. 1 may represent a portion of the data set that is stored and/or provided by an entity serving as a service provider, such as a hospital, a doctor's office, a clinical laboratory, and a pharmacy. Each entity may host, use, and/or manage one or more components, such as a data service that interoperates with the data services of other service providers to exchange data relating to the patient population.

The storage device 102 also includes a custom dictionary 114 and a natural language processing (NLP) model 116. For example, the custom dictionary 114 may store specific attribute name mappings between attribute names of different ones of the data lake model(s) 108, de-normalized data zone model(s) 110, and subscribing client entity model(s) 112. The natural language processing model 116 may include any suitable machine learning model for predicting attribute name mappings between different ones of the data lake model(s) 108, de-normalized data zone model(s) 110, and subscribing client entity model(s) 112, such as an NLP-based fuzzy logic algorithm (e.g., the fuzzyuzzy Python library that uses Levenshtein distance to calculate a difference between sequences).

A system administrator may interact with the storage device 102 to implement the attribute name mapping process via a user device 106. For example, the user device 106 may receive a selection of source and destination models, allow a system administrator to update the custom dictionary 114, supply an output attribute name mapping table, etc. The user device 106 may include any suitable device for receiving input and supplying attribute name mapping outputs to a user, such as a desktop computer, a laptop computer, a tablet, a smartphone, etc. The user device 106 may access the storage device 102 directly, or may access the storage device 102 through one or more networks 104. Example networks may include a wireless network, a local area network (LAN), the Internet, a cellular network, etc.

Figure 2:
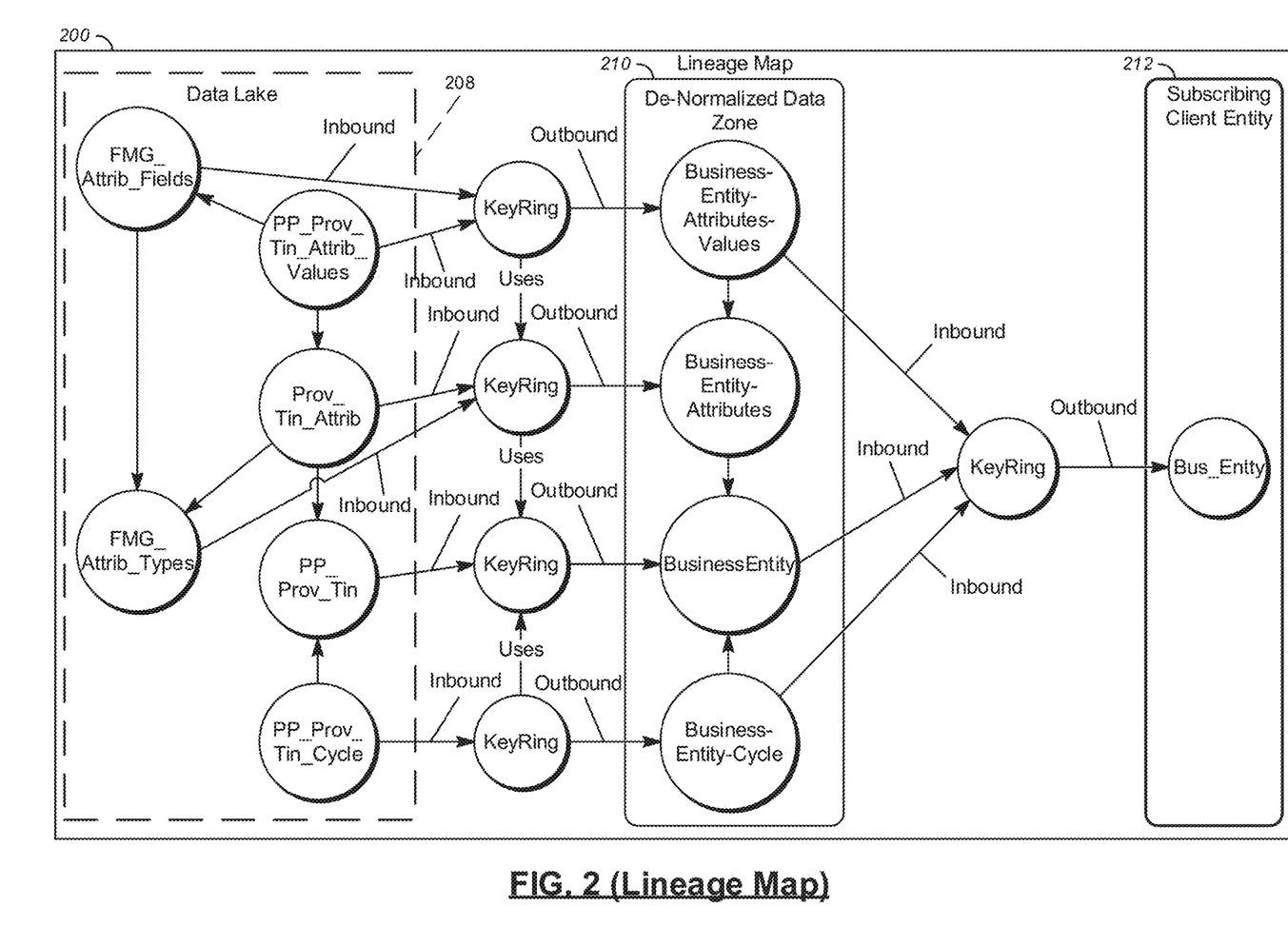
FIG. 2 is an illustration of an example attribute name map that may be presented as a visual depiction of example mapping of attribute names between source and destination models.

FIG. 2 illustrates an example an example attribute name lineage map 200 that may be presented as a visual depiction of example mapping of attribute names between models. The map 200 illustrates a data lake model 108 (broadly, a first database schema), a de-normalized data zone model 110 (broadly, a second database schema), and a subscribing client entity model 112 (broadly, a third database schema. The models 108, 110 and 112 may be similar to the models, 108, 110 and 112 of FIG. 1, respectively.

The map 200 illustrates inbound and outbound data flows between the data lake model 208, the de-normalized data zone model 210, and the subscribing client entity model 212. For example, names of resource attributes (e.g. FMG_Attrib_Fields) may be transformed by KeyRings as they are linked from the data lake model 208 to the de-normalized data zone model 210, and from the de-normalized data zone model 210 to the subscribing client entity model 212. In FIG. 2, the data lake model 208 may be considered as a data source view, the de-normalized data zone model 210 may be considered as an abstract data view of intermediate transformations of the data, and the subscribing client entity model 212 may be considered as a consumer specific view that will be presented to a consumer.

The attribute name mapping model may be used to predict mappings between source attribute names in one of the models 208 or 210, and destination attribute names in another of the models 210 or 212. For example, the destination data model may include multiple attributes that correspond to attributes in the source data model but have different attribute names (e.g., the data models have are used in the same context, relate to similar data, etc.). The attribute name mapping model could predict mappings of attribute names from the data lake model 208 to the de-normalized data zone model 210, from the de-normalized data zone model 210 to the subscribing client entity model 212, or from the data lake model 208 to the subscribing client entity model 212. Although FIGS. 1 and 2 each illustrate three data models, various implementations could include more or less data models, other types of data models, etc.

Attribute Name Mapping Process

Figure 3:
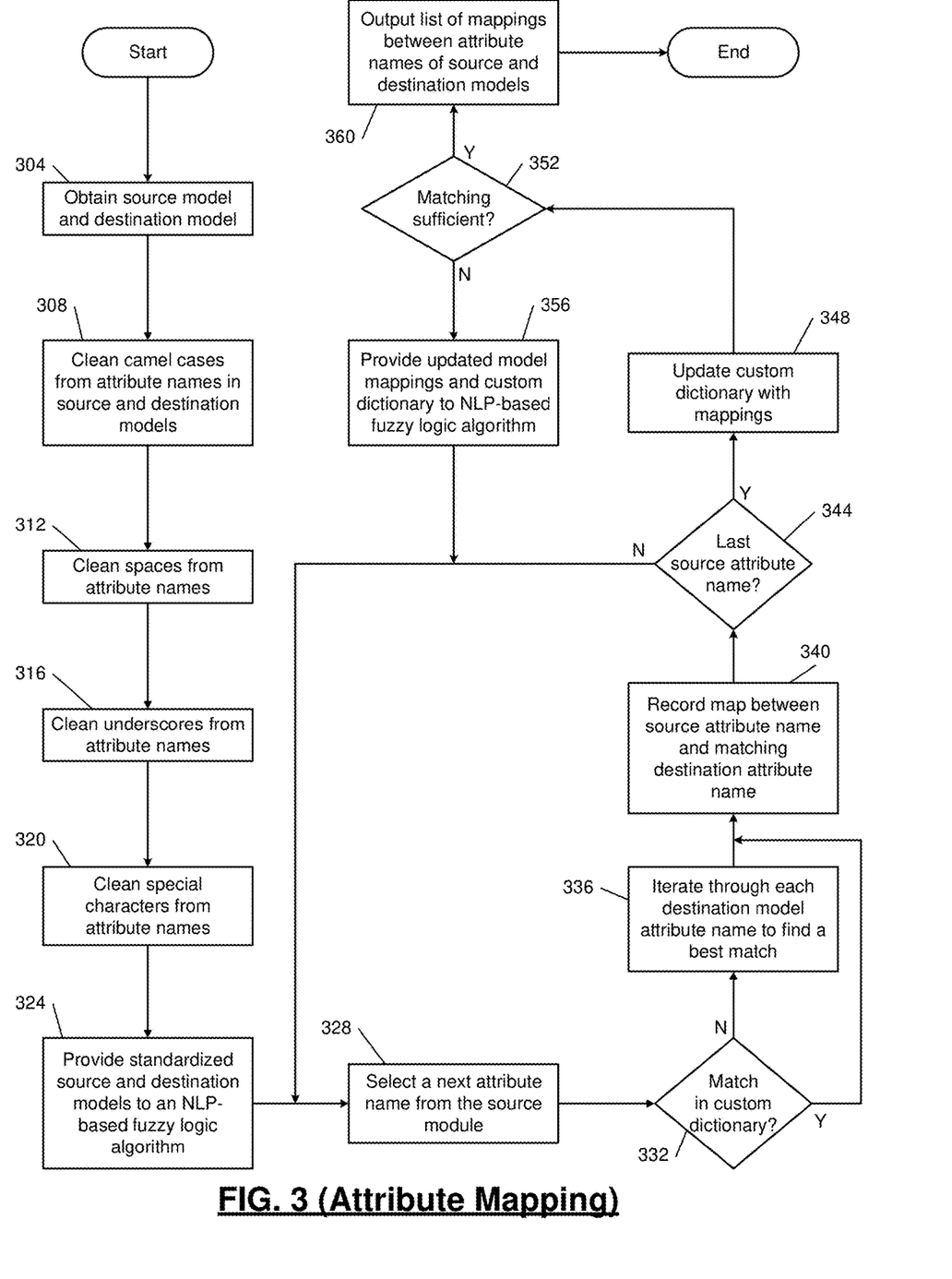
FIG. 3 is a flowchart depicting an example method for mapping attribute names between source and destination models.

FIG. 3 is a flowchart depicting an example method of mapping attribute names between a source model and a destination model. Although the example method is described below with respect to the attribute name mapping system of FIG. 1, the method may be implemented in other devices and/or systems.

In FIG. 3, control beings at 304, where control obtains a source model and a destination model from different bounded contexts in a distributed data storage system. For example, the source model may be one of the data lake model(s) 108 or de-normalized data zone model(s) 110 of the system of FIG. 1, and the destination model may be one of the de-normalized data zone model(s) 110 or subscribing client entity model(s) 112 of the system of FIG. 1.

At 308, control cleans camel cases from attribute names in the source model and the destination model. Camel cases (e.g., camelCase, camel caps or medial capitals) may include phrases where each word or abbreviation in the middle of the phrase begins with a capital letter, with no intervening spaces or punctuation. Common examples include "iPhone" and "eBay", and camel case is often used for variable names in computer programming to make multi-word attribute names more legible.

However, differences in camel case conventions (e.g., every word capitalized, first word not capitalized, etc.), and different use of camel case is different data models, may reduce the likelihood of exact matches between similar attribute names in different models. Standardizing the camel cases by removing capital letters so all attribute names are lower case, etc., may increase the likelihood of predicting correct attribute name matches between different source and destination models.

Control then proceeds to clean spaces from attribute names in the source and destination models at 312. For example, some attribute names may include spaces between words while other attribute names join words together without any spacing. Removing spaces from attribute names in the source and destination models may increase the likelihood of predicting correct attribute name matches between different source and destination models.

At 316, control removes underscores from the source and destination model attribute names. Similar to the spaces described at 312, some attribute names may separate words with an underscore character, while other similar attribute names may join words together without an underscore. Removing underscores from attribute names in the source and destination models may increase the likelihood of predicting correct attribute name matches between different source and destination models.

Control then proceeds to 320 to clean special characters from attribute names. For example, some attribute names may include symbols, punctuation, etc. that other similar attribute names do not. Removing special characters from attribute names in the source and destination models may increase the likelihood of predicting correct attribute name matches between different source and destination models.

Although FIG. 3 illustrates four specific cases of standardizing the source and destination models (i.e., camel cases, spaces, underscores and special characters), various implementations may uses more or less (or other) cleaning processes to standardize the attribute names. When the attribute names are standardized by removing potential differences in the formatting of the attribute names, the remaining letters, characters, etc. of the attribute names in the source and destination models may be more similar, leading to a higher likelihood of attribute name mapping model predicting correct matches.

At 324, control proves the standardized source and destination model attribute names to a machine learning model, such as an NLP-based fuzzy logic algorithm. The machine learning model may include any suitable machine learning network, such as a neural network, a long short-term memory network, a sequence-processing transformer, etc.

Control proceeds to select a next attribute name from the source model at 328. The machine learning model may start with the first attribute name from the source model and predict a best match from the destination attribute names, then iteratively proceed through each remaining attribute name in the source model until it reaches the end of the source model attribute names.

For example, at 322 control determines whether a match for the current source model attribute name exists in the custom dictionary. If a match exists, control will record a mapping between the current source model attribute name and the destination model attribute name match from the custom dictionary, at 340.

If a match does not exist in the custom dictionary at 322, control will iterate through each destination model attribute name to find a best match for current source attribute name, at 336. For example, control may run the machine learning model to determine the destination model attribute name having the highest match likelihood with the current source attribute name. Control then records a mapping between the source attribute name and the matching destination attribute name at 340. In various implementations, a match percentage may be returned based on a confidence interval (e.g., a determination of a percentage likelihood of matching between the source attribute name and matched destination attribute name, etc.).

At 344, control determines whether the last attribute name in the list of source model attribute names has been reached (e.g., if all source model attribute names have been mapped or at least attempted to match through the mapping process). If there are more source attribute names remaining, control returns to 328 to select a next attribute name from the source model for mapping processing.

If all source model attribute names have been processed at 344, control proceeds to 348 to update the custom dictionary with any mappings that were poorly determined or identified by the machine learning model, by any mappings that are erroneous as determined by a system administrator, etc. For example, an output of the predicted mappings may be provided to a system administrator, and the system administrator may review to determine whether any erroneous mappings have occurred.

Additionally, or alternatively, the output may flag attribute names that were not matched or had a matching likelihood below a threshold, and the system administrator may manually assign mappings to those unmatched attribute names. Therefore, the machine learning model may provide initial mappings to save time and increase efficiency of matching attribute names between different models, while allowing a system administrator to fine tune the mappings manually.

At 352, control determines whether the current output of mappings between the source and destination models is sufficient. For example, the model may require every source attribute name to be mapped to a destination attribute name, may require a percentage of mappings above a threshold, may require confirmation by a system administrator reviewer, etc.

If the matching is determined to be insufficient at 356, control proceeds to provide updated model mappings and the updated custom dictionary to the machine learning model at 356, and returns to 328 to select the first source attribute name in order to iterate through the list of source attribute names again in an effort to increase the success of the attribute name mapping. If the mapping is sufficient at 352, control proceeds to 360 to output a list of mappings between the source and destination models. The output mapping list may be consumed by an application that called the attribute name mapping model, may be displayed for review by a system administrator, etc.

Figure 4:
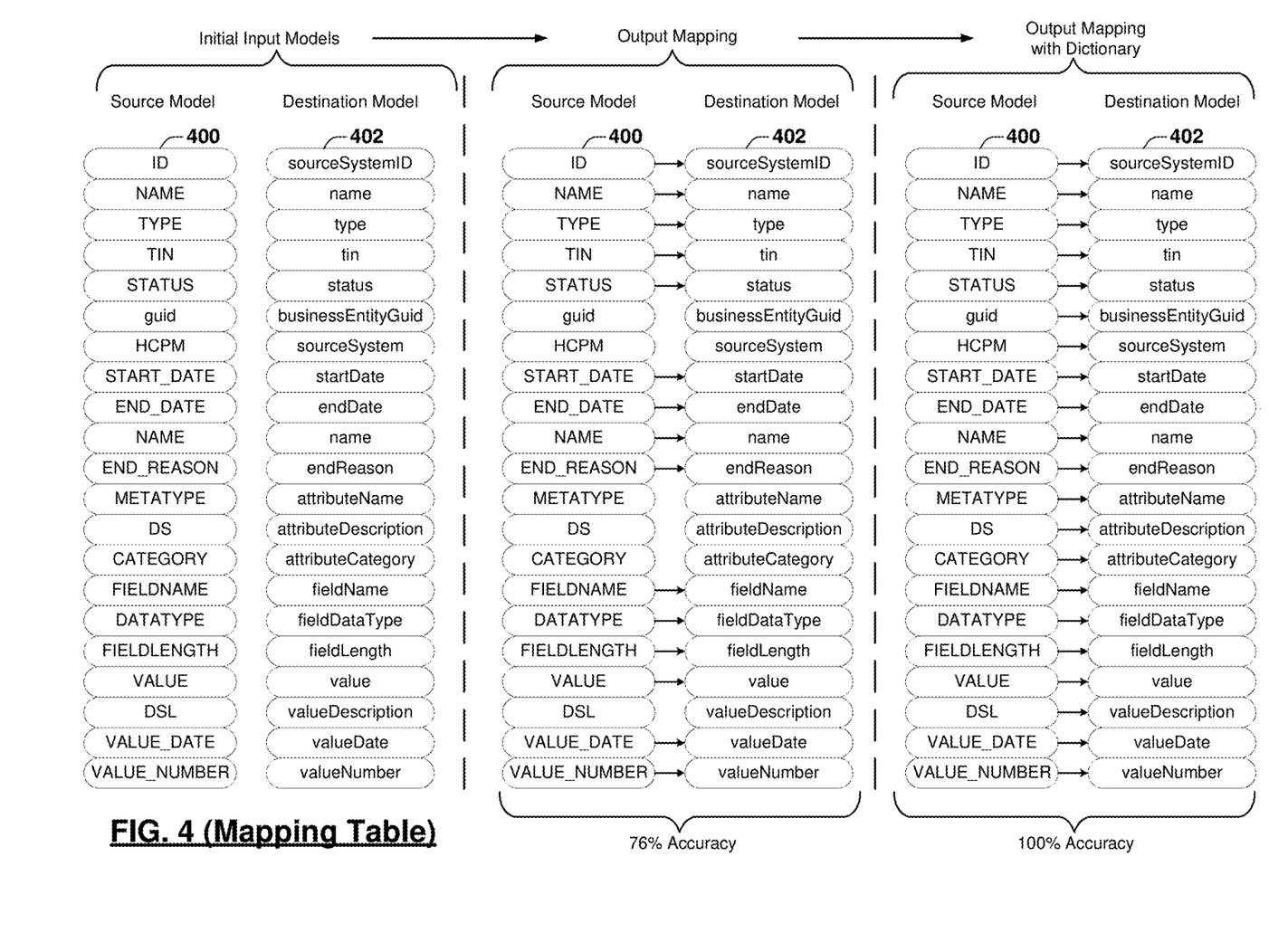
FIG. 4 is an illustration of example mapping tables during an example process of mapping attribute names between source and destination models.

FIG. 4 illustrates an example attribute name mapping table as the model moves from an initial state, to an output mapping based on the NLP-based algorithm, to output mapping that relies on the custom dictionary in addition to the NLP-based model. For example, in the initial input the source model attribute names 400 do not have any mapped relationships with the destination model attribute names 402.

After the attribute name mapping model performs a first round of mapping predictions using the NLP-based model algorithm, the source model attribute names 400 are mapped to the destination model attribute names 402 with 76% accuracy. As shown in the example of FIG. 4, the source model attribute names 'ID' and 'NAME' are successfully mapped to the destination model attribute names 'sourceSystemID' and 'name'. However, the NLP-based model algorithm was unable to map the source model attribute names 'guid' and 'HCPM' to the destination model attribute names 'businessEntityGuid' and 'sourceSystem'.

The rightmost section of FIG. 4 illustrates the mapping table after the custom dictionary is combined with the NLP-based algorithm results. As shown in FIG. 4, 100% accuracy indicates that each source model attribute name has been mapped to a destination model attribute name. For example, after the NLP-based algorithm indicates that some of the source model attribute names have not been mapped to destination model attribute names sufficiently, a system administrator may review the unmapped attribute names and then update the custom dictionary to include a mapping of 'guid' to 'businessEntityGuid', and a mapping of 'HCPM' to 'sourceSystem'.

Machine Learning Network

Figure 5:
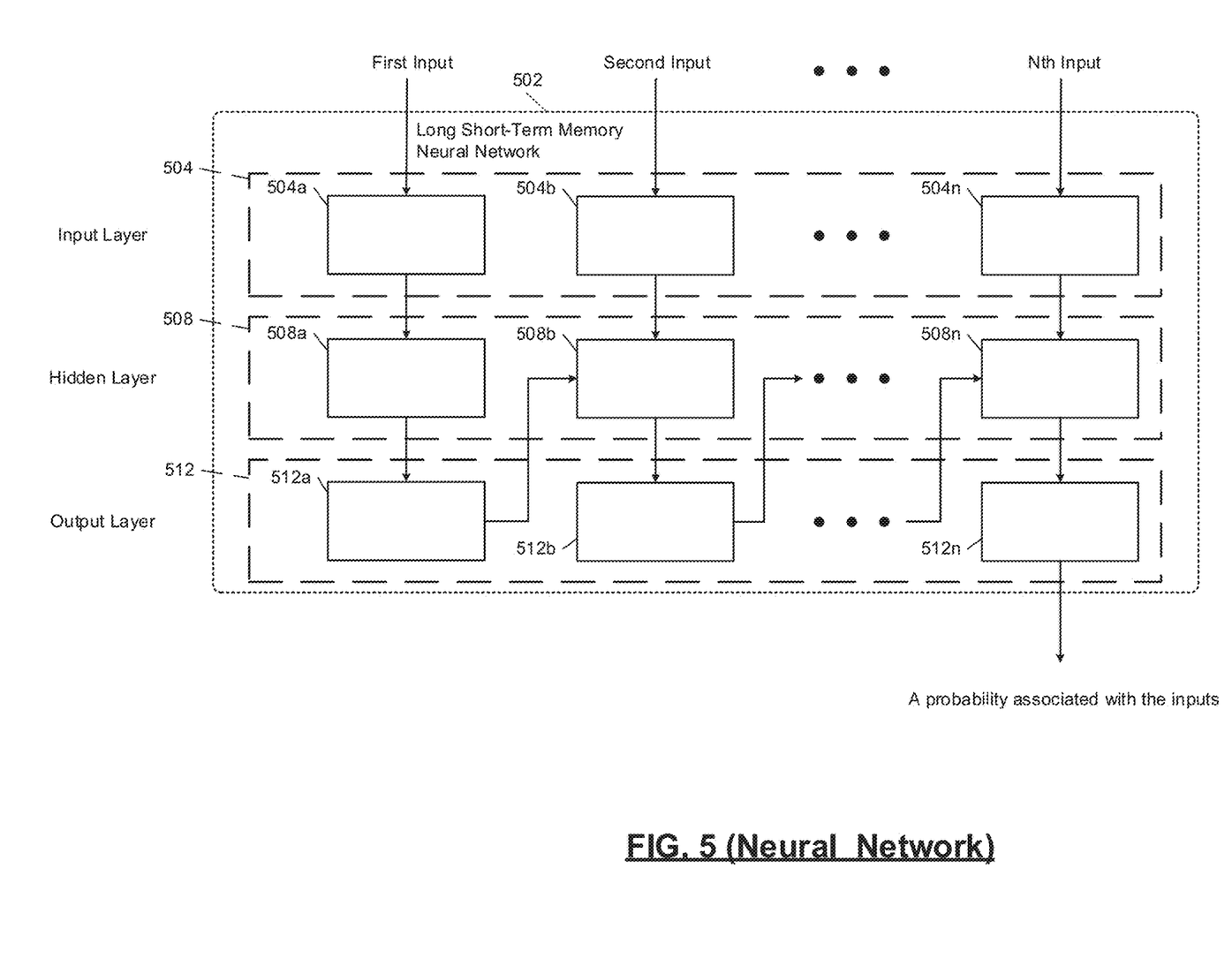
FIG. 5 is a functional block diagram of an example long short-term memory neural network.

FIG. 5 is a functional block diagram of a generic example LSTM neural network 502. The generic example LSTM neural network 502 may be used to implement the machine learning network of the attribute name mapping process of FIG. 3, although various implementations may use other types of machine learning networks. The LSTM neural network 502 includes an input layer 504, a hidden layer 508, and an output layer 512. The input layer 504 includes inputs 504a, 504b . . . 504n. The hidden layer 508 includes neurons 508a, 508b . . . 508n. The output layer 512 includes outputs 512a, 512b . . . 512n.

Each neuron of the hidden layer 508 receives an input from the input layer 504 and outputs a value to the corresponding output in the output layer 512. For example, the neuron 508a receives an input from the input 504a and outputs a value to the output 512a. Each neuron, other than the neuron 508a, also receives an output of a previous neuron as an input. For example, the neuron 508b receives inputs from the input 504b and the output 512a. In this way the output of each neuron is fed forward to the next neuron in the hidden layer 508. The last output 512n in the output layer 512 outputs a probability associated with the inputs 504a-504n. Although the input layer 504, the hidden layer 508, and the output layer 512 are depicted as each including three elements, each layer may contain any number of elements.

In various implementations, each layer of the LSTM neural network 502 must include the same number of elements as each of the other layers of the LSTM neural network 502. For example, attribute names in the source data model and output data model may be processed to create the inputs 504a-504n. The output of the LSTM neural network 502 may represent a destination model attribute name having the highest probability of matching the current source model attribute name.

In some embodiments, a convolutional neural network may be implemented. Similar to LSTM neural networks, convolutional neural networks include an input layer, a hidden layer, and an output layer. However, in a convolutional neural network, the output layer includes one fewer output than the number of neurons in the hidden layer and each neuron is connected to each output. Additionally, each input in the input layer is connected to each neuron in the hidden layer. In other words, input 504a is connected to each of hidden layer 508a, 508b, . . . 508n.

Message Sequence Chart

Figure 6:
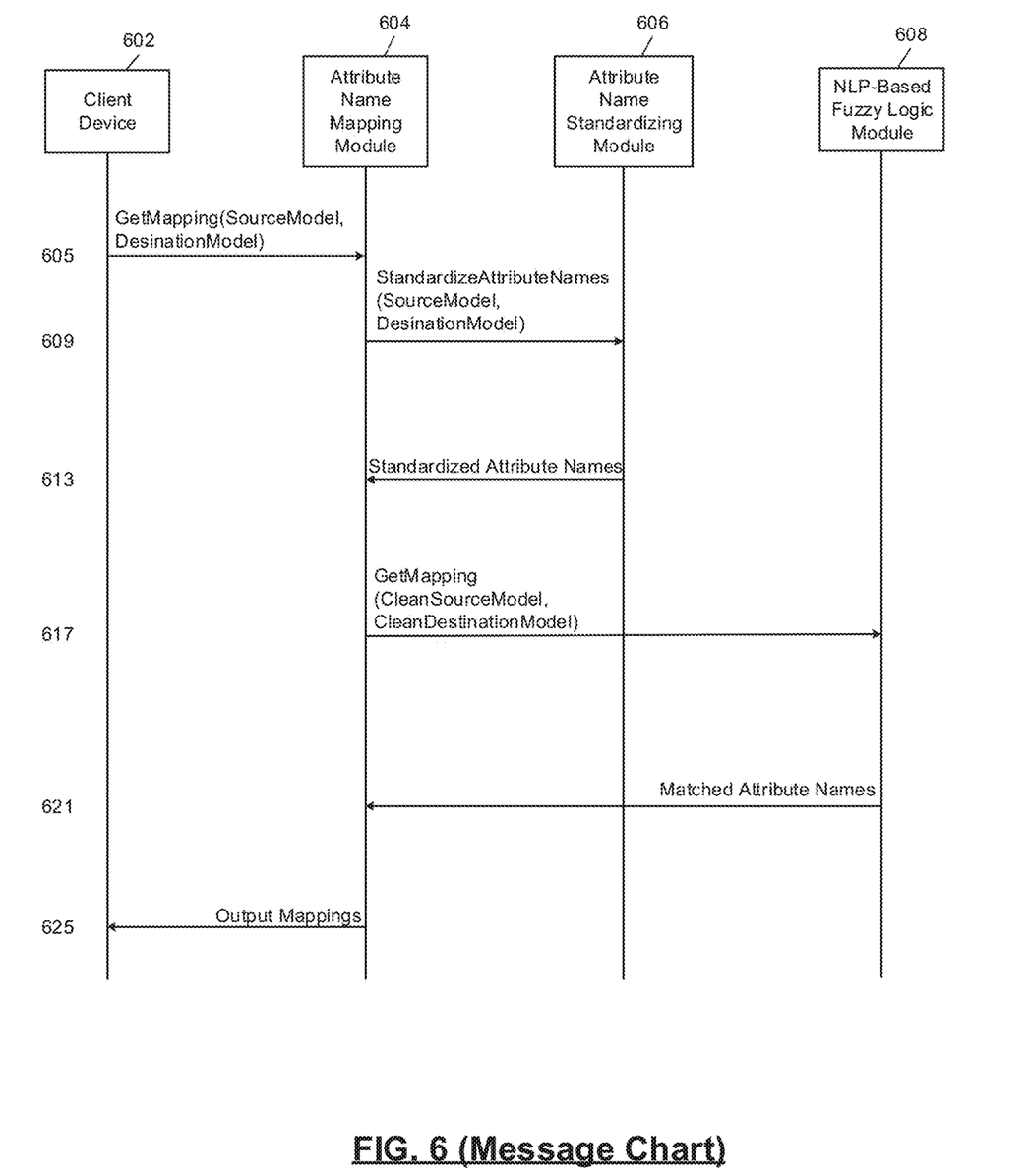
FIG. 6 is a message sequence chart showing example interactions between components of an attribute name mapping system for mapping attribute names between source and destination data models.

In FIG. 6, example interactions between a client device 602, an attribute name mapping module 604, an attribute name standardizing module 606 and an NLP-based fuzzy logic module 608 are illustrated, during a process of mapping attribute names from a source data model to a destination data model. At 605, the client device 602 calls the attribute name mapping module 604 to start the attribute name mapping process.

At 609, the attribute name mapping module 604 calls the attribute name standardizing model 606 in order to clean the attribute names of the source and destination data models. For example, the attribute name standardizing model 606 may process the source and destination attribute names to remove camel cases, spaces, underscores, special characters, etc. At 613, the standardized attribute names are then returned to the attribute name mapping module 604.

At 617, the attribute name mapping module 604 calls the NLP-based fuzzy logic module 608 in order to obtain a mapping of the source and destination model attribute names. For example, the module 608 may perform a machine learning algorithm in order to predict the most likely destination attribute name match for each source attribute name.

At 621, the module 608 supplies the matched attribute name mappings to the attribute name mapping module 604. At 625, the attribute name mapping module 604 supplies the output mappings (e.g., an output mapping table such as the one shown in FIG. 4, etc.) to the client device 602. The output mappings may then be used by an application on the client device 625 that called the attribute name mapping module 604, the output mappings may be displayed to a system administrator for review, etc.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. The phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computerized method of mapping attribute names of a source data model to a destination data model, the method comprising:
    obtaining multiple source attribute names from the source data model;
    obtaining multiple destination attribute names from the destination data model, wherein the destination data model includes multiple attributes that correspond to attributes in the source data model having different attribute names;
    processing the obtained source attribute names and the obtained destination attribute names to standardize the attribute names according to specified character formatting;
    supplying the standardized attribute names to a machine learning network model to predict a mapping of each source attribute name to a corresponding one of the destination attribute names;
    outputting, according to mapping results of the machine learning network model, an attribute mapping table indicating the predicted destination attribute name corresponding to each source attribute name; and
    in response to determining that the machine learning network model is unable to predict a mapping for one of the source attribute names:
        obtaining a matching input from a user identifying one of the destination attribute names that corresponds to an unmapped source attribute name; and
        updating a custom dictionary to include the matching input obtained from the user,
    wherein supplying the standardized attribute names to the machine learning network model includes:
        determining whether any of the source attribute names have an existing entry in the custom dictionary;
        for each source attribute name that has an existing entry in the custom dictionary, recording an output mapping for the source attribute name according to the existing entry in the custom dictionary; and
        for each source attribute name that does not have an existing entry in the custom dictionary, using the machine learning model to predict the mapping of each source attribute name to the corresponding one of the destination attribute names.

2. The method of claim 1, further comprising repeating multiple cycles of processing each source attribute name by predicting a corresponding destination attribute name using the machine learning network model or identifying a matching existing entry in the custom dictionary, until the attribute mapping table includes a mapped destination attribute name for a threshold number of source attribute names.

3. The method of claim 2, wherein the threshold number of source attribute names includes one hundred percent of the source attribute names.

4. The method of claim 1, wherein supplying the standardized attribute names to a machine learning network model includes:
    selecting a first one of the source attribute names and using the machine learning network model to identify one of the destination attribute names having a highest likelihood of correspondence with the selected first source attribute name;
    recording a mapping of the selected first source attribute name to the identified destination attribute name; and
    iteratively proceeding through remaining source attribute names to identify and record a corresponding destination attribute name for each source attribute name and returning a match percentage based on a confidence interval.

5. The method of claim 1, wherein processing the obtained source attribute names and the obtained destination attribute names to standardize the attribute names includes at least one of:
    removing camel cases from the source attribute names and the destination attribute names;
    removing spaces from the source attribute names and the destination attribute names;
    removing underscores from the source attribute names and the destination attribute names; and
    removing special characters from the source attribute names and the destination attribute names.

6. The method of claim 1, wherein the machine learning network model includes a natural language processing (NLP)-based algorithm.

7. The method of claim 1, wherein the machine learning network model includes a long short-term memory (LSTM) network.

8. The method of claim 1, wherein the source data model and the destination data model belong to different database schemas within a distributed data storage system.

9. The method of claim 8, wherein the source data model belongs to one of a data lake bounded context and a de-normalized data zone bounded context of a health care publisher platform, and the destination model belongs to one of the de-normalized data zone bounded context and a subscribing client entity bounded context of the health care publisher platform.

10. A computer system comprising:
    memory configured to store a source data model, a destination data model, a machine learning network model, and computer-executable instructions and
    at least one processor configured to execute the instructions, wherein the instructions include:
        obtaining multiple source attribute names from the source data model;
        obtaining multiple destination attribute names from the destination data model, wherein the destination data model includes multiple attributes that correspond to attributes in the source data model having different attribute names;
        processing the obtained source attribute names and the obtained destination attribute names to standardize the attribute names according to specified character formatting;

supplying the standardized attribute names to a machine learning network model to predict a mapping of each source attribute name to a corresponding one of the destination attribute names;

outputting, according to mapping results of the machine learning network model, an attribute mapping table indicating the predicted destination attribute name corresponding to each source attribute name; and in response to determining that the machine learning network model is unable to predict a mapping for one of the source attribute names:

receiving a matching input from a user identifying one of the destination attribute names that corresponds to an unmapped source attribute name; and updating a custom dictionary to include the matching input received from the user, wherein supplying the standardized attribute names to the machine learning network model includes:

determining whether any of the source attribute names have an existing entry in the custom dictionary;

for each source attribute name that has an existing entry in the custom dictionary, recording an output mapping for the source attribute name according to the existing entry in the custom dictionary; and for each source attribute name that does not have an existing entry in the custom dictionary, using the machine learning network model to predict the mapping of the source attribute name to the corresponding one of the destination attribute names.

11. The computer system of claim 10, wherein the instructions include repeating multiple cycles of processing each source attribute name by predicting a corresponding destination attribute name using the machine learning network model or identifying a matching existing entry in the custom dictionary, until the attribute mapping table includes a mapped destination attribute name for a threshold number of source attribute names.

12. The computer system of claim 11, wherein the threshold number of source attribute names includes one hundred percent of the source attribute names.

13. The computer system of claim 10, wherein supplying the standardized attribute names to a machine learning network model includes:

selecting a first one of the source attribute names and using the machine learning network model to identify one of the destination attribute names having a highest likelihood of correspondence with the selected first source attribute name;

recording a mapping of the selected first source attribute name to the identified destination attribute name; and iteratively proceeding through remaining source attribute names to identify and record a corresponding destination attribute name for each source attribute name and returning a match percentage based on a confidence interval.

14. The computer system of claim 10, wherein processing the obtained source attribute names and the obtained destination attribute names to standardize the attribute names includes at least one of:

removing camel cases from the source attribute names and the destination attribute names;

removing spaces from the source attribute names and the destination attribute names;

removing underscores from the source attribute names and the destination attribute names; and removing special characters from the source attribute names and the destination attribute names.

15. The computer system of claim 10, wherein the source data model and the destination model belong to different database schemas within a distributed data storage system.

16. The computer system of claim 15, wherein the source data model belongs to one of a data lake bounded context and a de-normalized data zone bounded context of a health care publisher platform, and the destination model belongs to one of the de-normalized data zone bounded context and a subscribing client entity bounded context of the health care publisher platform.

* * * * *